United States Patent
Qian et al.

(10) Patent No.: US 9,657,017 B2
(45) Date of Patent: May 23, 2017

(54) CRYSTAL FORM OF (R)-PRAZIQUANTEL AND PREPARATION METHOD AND APPLICATION THEREOF

(71) Applicant: TONGLI BIOMEDICAL CO., LTD., Zhangjiagang, Jiangsu (CN)

(72) Inventors: Mingxin Qian, Jiangsu (CN); Rodney JY Ho, Jiangsu (CN); Chunsheng Qiao, Jiangsu (CN); Junwei Shi, Jiangsu (CN)

(73) Assignee: Tongli Biomedical Co., Ltd. (CN)

( * ) Notice: Subject to any disclaimer, the term of this patent is extended or adjusted under 35 U.S.C. 154(b) by 0 days.

(21) Appl. No.: 15/029,991

(22) PCT Filed: Oct. 16, 2014

(86) PCT No.: PCT/CN2014/088700
§ 371 (c)(1),
(2) Date: Apr. 15, 2016

(87) PCT Pub. No.: WO2015/055126
PCT Pub. Date: Apr. 23, 2015

(65) Prior Publication Data
US 2016/0272636 A1 Sep. 22, 2016

(30) Foreign Application Priority Data

Oct. 17, 2013 (CN) .......................... 2013 1 0488773

(51) Int. Cl.
*A61K 31/4985* (2006.01)
*C07D 487/04* (2006.01)
*C07D 471/04* (2006.01)

(52) U.S. Cl.
CPC ........ *C07D 471/04* (2013.01); *C07B 2200/13* (2013.01)

(58) Field of Classification Search
CPC .......................... A61K 31/4985; C07D 487/04
USPC .......................................... 514/250; 544/344
See application file for complete search history.

(56) References Cited

FOREIGN PATENT DOCUMENTS

| CN | 102911979 A | 2/2013 |
| CN | 103160562 A | 6/2013 |
| CN | 103333931 A | 10/2013 |

OTHER PUBLICATIONS

El-Arini, et al. Pharmaceutical Development and Technology, 3(4), 1998, 557-564.*
Lewandowski, et al. Langmuir, 26(18), 2010, 14671-14679.*

* cited by examiner

*Primary Examiner* — Douglas M Willis
(74) *Attorney, Agent, or Firm* — Connie Ding; Peter L. Brewer; Baker Donelson IP Group (57) ABSTRACT

The present invention relates to a crystal form of (R)-praziquantel and a preparation method and uses thereof. The X-ray diffraction pattern (CuKα radiation) of the crystal form of (R)-praziquantel at 25° C. shows the following diffraction peaks: 2-Theta =6.9±0.2°, 8.3±0.2°, 15.1±0.2°, 17.4±0.2°, 19.8±0.2°, 21.9±0.2°, 24.3 ±0.2° or d=12.74±0.20 Å, 10.61±0.20 Å, 5.87±0.20 Å, 5.09±0.20 Å, 4.48±0.20 Å, 4.06±0.20 Å, 3.66±0.20 Å. Compared to the existing crystal form of praziquantel, the crystal form of the present invention has better solubility, better drug efficacy and better pharmacokinetic characteristics. The preparation method of the present invention has the following advantages: good reproducibility, environmentally friendly, low cost, and able to operate at a normal pressure and temperature, and suitable for large-scale production.

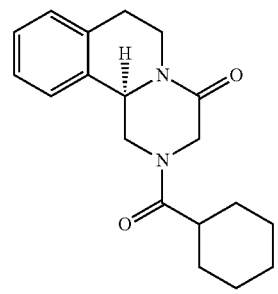

(R)-Praziquantel

11 Claims, 5 Drawing Sheets

CRYSTAL FORM OF (R)-PRAZIQUANTEL AND PREPARATION METHOD AND APPLICATION THEREOF

CROSS REFERENCE TO RELATED APPLICATIONS

This application is a §371 National State Application of PCT/CN2014/088700 filed Oct. 16, 2014, which claims priority to CN 201310488773.4 filed Oct 17, 2013, which are hereby incorporated by reference in their entirety.

TECHNICAL FIELD

The present invention relates to a crystal form of (R)-praziquantel, the preparation method thereof, and applications thereof in the drugs treating parasitic diseases. In addition, the present invention also relates to a product that prepared by taking the crystal form of (R)-praziquantel as an active component, which includes, but not limited to, an active pharmaceutical ingredient, a formulation, a premix, a healthcare product and the like.

BACKGROUND

Praziquantel is a synthesized pyrazine isoquinoline derivative, also called cyclo-praziquantel, and a white or off-white crystalline powder and bitter in taste. It is worldwide recognized as a highly effective and broad-spectrum anti-parasite drug and widely used for treating diseases such as *schistosomiasis japonica, schistosomiasis haematobium, schistosomiasis mansoni, clonorchiasis, paragonimiasis, sparganosis mansoni, fasciolopsis, echinococcosis, taeniasis, cysticercosis*, etc. It has advantages such as broad anti-parasitic spectrum, high efficacy, low toxicity, short therapeutic course and easy to use, etc. In addition to human use, it is also widely used in anti-parasitic treatment of animals including poultry and livestock. The invention of praziquantel is a major breakthrough in the history of anti-parasitic chemotherapy. In the past 30 years, praziquantel has still been the first choice of drug for treating various parasitic diseases on the market.

Praziquantel is a racemic compound composed of (R)-praziquantel and (S)-praziquantel together. Scientists have separated and obtained both pure optic isomers of (R)-praziquantel and (S)-praziquantel from synthesized praziquantel, and found in preclinical studies and preliminary clinical trials that: (R)-praziquantel is the active parasiticidal component of praziquantel, while the (S)-praziquantel is inactive or even harmful; at the same dosage, the clinical efficacy of (R)-praziquantel is better than that of praziquantel, and (S)-praziquantel has little activity, bitter taste and is the major source of drug side effects; (R)-praziquantel shows lower cardiac toxicity than (S)-praziquantel. Therefore, the development of (R)-praziquantel has clinical application values of higher efficacy, less side effects, and better medical compliance.

Chinese invention patent publication number CN102786520A discloses a Form A of praziquantel and a preparation method and application thereof. The reported praziquantel Form A shows that the Height %=100 peak is at the position where 2-Theta=20.0±0.2° or d=4.4±0.2 Å and 43 diffraction peaks exist when analyzed by powder X-ray diffraction.

Chinese invention patent publication number CN102786519A discloses a state of matter of Form B praziquantel, wherein the Height %=100 peak is at the position where 2-Theta=18.7±0.2° or d=4.7±0.2 Å in powder X-ray diffraction analysis.

SUMMARY OF THE INVENTION

The present invention is intended to provide a crystal form of (R)-praziquantel and a preparation method thereof.

The present invention further provides an application of the crystal form of (R)-praziquantel and a drug composition containing the crystal form of (R)-praziquantel.

To achieve the above technical aims, the present invention employs the following technical schemes:

A crystal form of (R)-praziquantel, wherein the X-ray diffraction pattern (CuKα radiation) of the crystal format 25° C. shows the following seven diffraction peaks: 2-Theta=6.9±0.2°, 8.3±0.2°, 15.1±0.2°, 17.4±0.2°, 19.8±0.2°, 21.9±0.2°, 24.3±0.2° or d=12.74±0.20 Å, 10.61±0.20 Å, 5.87±0.20 Å, 5.09±0.20 Å, 4.48±0.20 Å, 4.06±0.20 Å, 3.66±0.20 Å.

Further, the X-ray diffraction pattern (CuKα radiation) of the crystal form at 25° C. further shows the following fifteen diffraction peaks: 2-Theta=13.4±0.2°, 14.1±0.2°, 15.7±0.2°, 16.6±0.2°, 17.9±0.2°, 18.2±0.2°, 19.0±0.2°, 20.6±0.2°, 23.8±0.2°, 27.4±0.2°, 28.5±0.2°, 29.0±0.2°, 30.9±0.2°, 33.7±0.2°, 39.5±0.2° or d=6.59±0.20 Å, 6.29±0.20 Å, 5.63±0.20 Å, 5.33±0.20 Å, 4.96±0.20 Å, 4.86±0.20 Å, 4.68±0.20 Å, 4.31±0.20 Å, 3.74±0.20 Å, 3.25±0.20 Å, 3.13±0.20 Å, 3.07±0.20 Å, 2.89±0.20 Å, 2.66±0.20 Å, 2.28±0.20 Å.

Further, the X-ray diffraction pattern (CuKα radiation) of the crystal format 25° C. further shows the following five diffraction peaks: 2-Theta=8.67±0.2°, 23.0±0.2°, 25.4±0.2°, 27.8±0.2°, 32.4±0.2° or d=10.19±0.20 Å, 3.86±0.20 Å, 3.50±0.20 Å, 3.20±0.20 Å, 2.76±0.20 Å.

Figure 1:
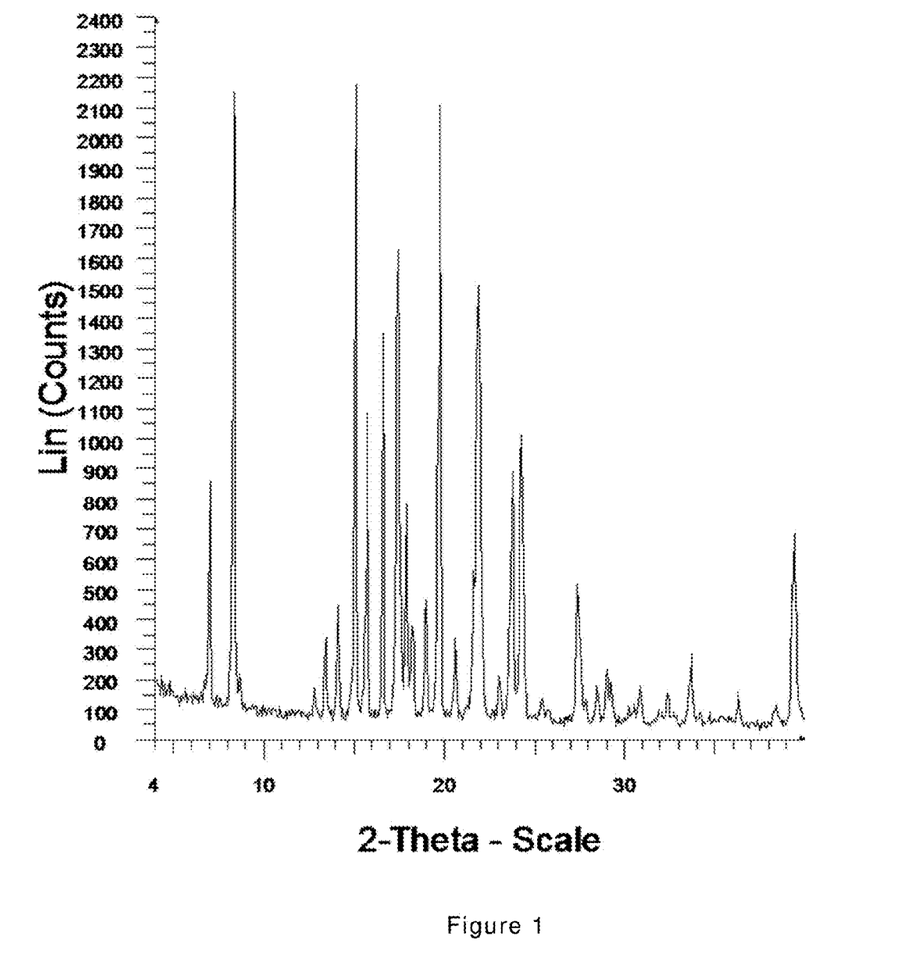
FIG. 1 is an X-ray powder diffraction spectrum of (R)-praziquantel crystal form.

According to one specific and preferred aspect, the X-ray diffraction pattern is shown in FIG. 1.

Further, the X-ray diffraction pattern shows 36 diffraction peaks, and peak positions and peak intensities thereof are listed in Table 1, wherein, the peak positions vary within ±0.2°.

Preferably, the thermogram of the crystal form measured by differential scanning calorimetry shows an absorption peak at the position of 111±3° C.; the melting point of the crystal form is 109±2° C. and the optical rotation of the crystal form $[\alpha]_D$) at 20° C. is −140.12° ($CH_3OH$).

Figure 5:
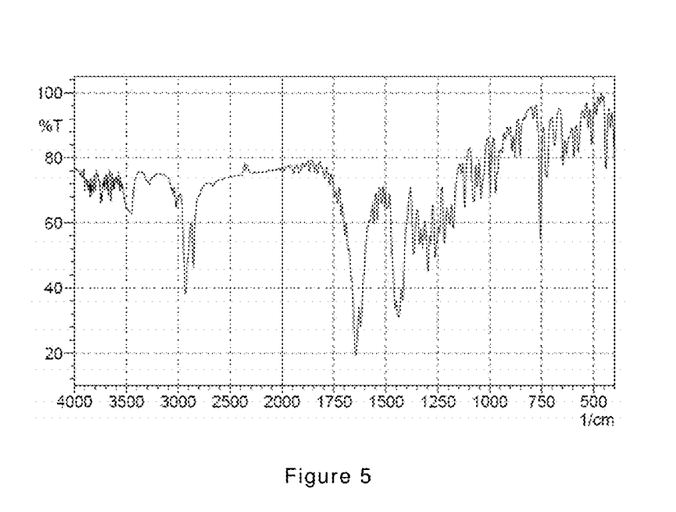
FIG. 5 is an infrared absorption spectrum of (R)-praziquantel crystal form.

According to the present invention, the infrared absorption spectrum of the crystal form shows absorption peaks at 3460 $cm^{-1}$, 3277 $cm^{-1}$, 3065 $cm^{-1}$, 3048 $cm^{-1}$, 3021 $cm^{-1}$, 3003 $cm^{-1}$, 2932 $cm^{-1}$, 2853 $cm^{-1}$, 2660 $cm^{-1}$, 1651 $cm^{-1}$, 1645 $cm^{-1}$, 1622 $cm^{-1}$, 1576 $cm^{-1}$, 1570 $cm^{-1}$, 1558 $cm^{-1}$, 1541 $cm^{-1}$, 1533 $cm^{-1}$, 1522 $cm^{-1}$, 1506 $cm^{-1}$, 1497 $cm^{-1}$, 1489 $cm^{-1}$, 1472 $cm^{-1}$, 1456 $cm^{-1}$, 1437 $cm^{-1}$, 1418 $cm^{-1}$, 1387 $cm^{-1}$, 1364 $cm^{-1}$, 1339 $cm^{-1}$, 1323 $cm^{-1}$, 1296 $cm^{-1}$, 1285 $cm^{-1}$, 1263 $cm^{-1}$, 1254 $cm^{-1}$, 1242 $cm^{-1}$, 1217 $cm^{-1}$, 1190 $cm^{-1}$, 1175 $cm^{-1}$, 1136 $cm^{-1}$, 1121 $cm^{-1}$, 1082 $cm^{-1}$, 1074 $cm^{-1}$, 1061 $cm^{-1}$, 1042 $cm^{-1}$, 1032 $cm^{-1}$, 997 $cm^{-1}$, 972 $cm^{-1}$, 962 $cm^{-1}$, 939 $cm^{-1}$, 924 $cm^{-1}$, 907 $cm^{-1}$, 893 $cm^{-1}$, 854 $cm^{-1}$, 831 $cm^{-1}$, 793 $cm^{-1}$, 756 $cm^{-1}$, 731 $cm^{-1}$, 723 $cm^{-1}$, 689 $cm^{-1}$, 648 $cm^{-1}$, 631 $cm^{-1}$, 594 $cm^{-1}$, 575 $cm^{-1}$, 546 $cm^{-1}$, 527 $cm^{-1}$, 509 $cm^{-1}$, 486 $cm^{-1}$, 473 $cm^{-1}$, 457 $cm^{-1}$, 442 $cm^{-1}$ and 409 $cm^{-1}$, and the absorption peak positions vary within ±2 $cm^{-1}$. According to one specific aspect, the infrared absorption spectrum of the crystal form is shown in FIG. 5.

Furthermore, the solubility of the crystal form of (R)-praziquantel in water and in simulated gastro-intestinal fluid at the temperature of 25° C. ranges from 0.30~0.43 mg/mL.

Another technical scheme employed by the present invention is: the above preparation method of the crystal form of (R)-praziquantel which is obtained by using organic solvents to recrystallize (R)-praziquantel.

Further, (R)-praziquantel is added into the organic solvent and heated up to 20~60° C. to dissolve (R)-praziquantel; the solution is filtered, and the filtrate is kept and cooled down to 10~30° C. to crystallize, or added with an antisolvent, or the solvent is vacuum-removed to give a white solid, i.e. said crystal form of (R)-praziquantel.

The above mentioned organic solvent is selected from one or more of ethyl acetate, isopropyl acetate, methanol, ethanol, tetrahydrofuran and acetonitrile; the antisolvent is selected from one or more of water, toluene, n-heptane, cyclohexane and acetone.

According to one specific and preferred aspect of the present invention, the organic solvent is acetonitrile, and the antisolvent is acetone, toluene or a combination thereof. More preferably, the antisolvent is a combination of acetone and toluene, and the volume ratio of acetonitrile, acetone and toluene is 1:0.4~0.6:3~3.5.

Further, the method further includes the step of employing the following reaction to prepare (R)-praziquantel:

the above step of preparing (R)-praziquantel specifically includes: reacting compound 4H with benzyl triethyl ammonium chloride in the presence of dichloroethane solvent, alkali atrefluxing temperature; after the end of reaction, adding water and extracting with dichloromethane, washing the organic phase with water, 4 wt %-~6 wt % hydrochloric acid solution and NaCl saturated solution in proper order, drying over anhydrous sodium sulfate, evaporating the solvent, and purifying the residue with column chromatography on silica gel using an eluent of PE/EA=20:1~5:1 to give a concentrated product, i.e. (R)-praziquantel.

The above alkali may be sodium hydroxide or potassium hydroxide, etc.

The present invention further provides a product for preventing and/or treating parasitic diseases, the active component of which at least contains the above crystal form of (R)-praziquantel of the present invention.

According to the present invention, the product includes, but not limited to, an active pharmaceutical ingredient, a pharmaceutical formulation, a premix, and a healthcare product. In the product, the purity of (R)-praziquantel may be 1 wt %-100 wt %. In the product, (R)-praziquantel may be the only active ingredient, and also may be combined with one or more other active ingredients to compose a multi-formula product.

The present invention further provides a drug composition for preventing and/or treating parasitic diseases, which contains an active component and a pharmaceutically acceptable carrier, wherein the active component at least contains the crystal form of (R)-praziquantel.

Furthermore, the dosage form of the drug composition is tablets (including coated tablets, sugar-coated tablets, and dispersible tablets), capsules, pills, granules, syrups, aqueous solution injections, powder injections, premix, aerosols, suspensions, solvents or drug rods.

The solubility of the crystal form of (R)-praziquantel of the present invention in water and simulated gastro-intestinal fluid at the temperature of 25° C. ranges from 0.30~0.43 mg/mL, which are significantly higher than the solubility of praziquantel (0.19~0.31 mg/mL). This advantage is greatly favorable for pharmaceutical formulation development of the drug composition.

In addition, the present invention studied the anti-parasitic activity of the above (R)-praziquantel, and compared the efficacy of anti-*schistosomiasis japonica* between the crystal form of (R)-praziquantel and a crystal form of praziquantel employing an in vitro culture method. The results showed that both the crystal forms of (R)-praziquantel and praziquantel can induce contraction and paralysis of *schistosoma japonicum*, however, there was obviously difference between the intensity of inhibition on worm activity of them, and $IC_{50}$ of the crystal form of (R)-praziquantel is only ⅕ of that of praziquantel crystal form (P<0.01) (Table 4). The result confirmed that the crystal form of (R)-praziquantel has an apparently higher anti-parasitic activity on *schistosoma japonicum* than that of praziquantel crystal form.

For further confirming the anthelmintic effect of (R)-praziquantel crystal form, the curative effect of the (R)-praziquantel crystal form was studied in SD rat disease models artificially infected with *clonorchiasis sinensis*. Compared to the blank control group, the treatment group of (R)-praziquantel crystal form showed significant therapeutic effect (P<0.01) with the cure rate up to 100% and no worm body found in rat feces.

Figure 8:
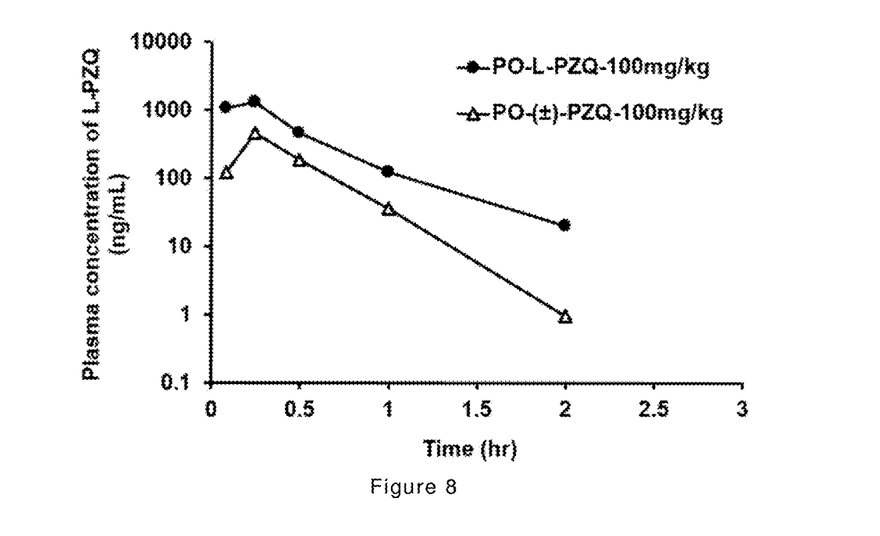
FIG. 8 is a comparison diagram of plasma concentration-time curves of (R)-praziquantel in mice after orally given with the same dose of (R)-praziquantel and praziquantel.

For further investigating the pharmacokinetics of products of (R)-praziquantel crystal form in animals, after giving the rats with an oral single dose at 75 mg/kg, the biologic disposition was as follow: the time to reach peak plasma concentration of (R)-praziquantel was 15 minutes, the peak plasma concentration of the drug was 3132±1440 ng/mL, the terminal half life was 0.89±0.19 h, and the area under plasma concentration-time curve was 3572±1793 h·ng/mL. Further comparing the blood concentration characteristics of (R)-praziquantel crystal form and praziquantel crystal form in mice after oral administration, the result showed that: after orally giving the mice with (R)-praziquantel and praziquantel at 100 mg/kg in the two groups of animals respectively, the peak plasma concentrations of (R)-praziquantel both were 15 minutes, the peak concentrations in plasma respectively were 1290 ng/mL and 464 ng/mL, and the areas under plasma concentration-time curves respectively were 667 h·ng/mL and 208 h·ng/mL(see FIG. 8). It was thus evident that, after giving the mice with the same oral dose of the drugs, the exposure and the peak plasma concentration of the effective component, i.e. (R)-praziquantel, in (R)-praziquantel crystal form group were apparently higher than those in praziquantel crystal form group, which offers the possibility of safe administration and enhanced therapeutic effect.

A product containing the crystal form of (R)-praziquantel as an active ingredient has a better solubility than that containing praziquantel, and would be beneficial to prepare the various formulations mentioned above, and ensures the absorption characteristics, the effective bioavailability, the effective plasma drug concentrations as well as the sustainable duration of effective plasma exposure in biological bodies, thus taking advantages in prevention, treatment and healthcare applications and the like.

The present invention also relates to uses of the crystal form of (R)-praziquantel in preparation of products for preventing and/or treating parasitic diseases.

The said parasitic diseases include human diseases and animal (pets, livestock, birds, fish and other aquatic animals) diseases.

The said parasitic diseases include a variety of trematodiasis (*schistosomiasis, clonorchiasis*, paragonimiasis, etc.) and various taeniasis.

A multi-formula product of the present invention combined with other anti-parasitic drugs also can be used for treating nematodiasis, trematodiasis, taeniasis, coccidiosis, trichinelliasis, filariasis, toxoplasmosis, malaria and the like.

Due to the implementation of the above technical schemes, the present invention has the following advantageous effects when compared to the prior art:

The present invention provides a crystal form of (R)-praziquantel which is apparently different from the already reported crystal form of praziquantel; the said crystal form of (R)-praziquantel has high purity, excellent physicochemical properties and good reproducibility, and also has stronger parasiticidal activity, better solubility and more characteristic pharmacokinetic properties than similar products of praziquantel crystal forms existing in current market, and thus provides the possibility to develop an anthelmintic drug composition and formulation product of human being and animals, which is more favorable clinically to achieve a more superior anti-parasitic efficacy and safety.

The present invention further provides a preparation technology of synthesizing (R)-praziquantel and a crystal form thereof. This technology has the advantages of green environmental protection, low cost, capable of operating under normal temperature and pressure, and easy for quality control. The crystallization method thereof can effectively improve the product quality, and can be effectively applied in drug composition preparation, and establishes a reliable foundation for large scale-up production of (R)-praziquantel.

DETAILED DESCRIPTION OF EMBODIMENTS

In the following, the present invention is explained in detail combing with the specific embodiments, however, the present invention is not limited to those embodiments.

Preparation of the Crystal Form of (R)-Praziquantel

The preparation of the crystal form of (R)-praziquantel includes the following steps:

(1) Step of preparing intermediate of formula 1 from compound of formula 2a:

in formulas 1, 2a and 2b, $X^+$ is the same, and represents counter cation portion of the carboxylic acid ions, and specifically is, for example, $H^+$, $K^+$, $Na^+$ or $NH_4^+$.

The method of preparing the intermediate of formula 1 is as follow: firstly, compound of formula 2a or 2b and oxygen generate oxidizing reaction under the existing of recombinant D-amino acid oxidase and catalase, and then, the resulted product of the oxidation reaction is reduced to give the intermediate of formula 1 under the action of borane-amine complex.

(2) Preparing (R)-praziquantel from intermediate of formula 1 according to the following route:

In the above formulas 3 to 7, R is the same, and represents amino protection group.

Example 1: Preparation of recombinant D-amino acid oxidase

Single colonies of recombinant *Escherichia coli* containing D-amino acid oxidase gene were inoculated from either a glycerol-containing tube or a transformation plate to a 4 mL LB liquid culture medium containing (100 μg/mL) ampicillin, and activated at 37° C. overnight for 12-16 hours. The activated culture was transferred to 100 mL liquid LB culture medium containing (100 μg/mL) ampicillin at an inoculum size of 2%, and shaking cultured at 37° C. and at 200 rpm until $OD_{600}$ reached about 0.6. An inducer isopropyl-β-d-thiogalactopyranoside was added to reach a final concentration of 0.8 mmol/L, and cultured overnight at 30° C. The culture was centrifuged (4° C., 5000 rpm, 15 min) to collect cells which were suspended with 10 mL of phosphate buffer (100 mM, pH 7.0). The cell suspension was sonicated in ice bath for 10 minutes and centrifuged (4° C., 12000 rpm, 15 min). The supernatant liquid was precooled overnight at −20° C., and then cryodesiccated for 34~40 hours to obtain the freeze-dried powdery and recombinant D-amino acid oxidase.

Example 2: Preparation of intermediate (R)-1,2,3,4-tetrahydroisoquinoline-1-carboxylic acid ammonium salt 1.77 g DL-1,2,3,4-tetrahydroisoquinoline-1-carboxylic acid (0.01 mol) was dissolved in 5 mL ammonia (adjusting pH to 8.0), and 1.5 g borane-ammonia complex (0.05 mol) was added. Oxygen was inlet at a uniform speed, and 88.5 mg recombination D-amino acid oxidase and 18 mg catalase were respectively added. Under the condition of stirring, the reaction was generated at 28° C. and the extent of the reaction was detected by HPLC. HPLC showed that after about 28 hours (S)-1,2,3,4-tetrahydroisoquinoline-1-carboxylic acid ammonium salt was less than 1%. The reaction was stopped, and the solution was heated to 50-60° C. for more than half an hour to denature the enzyme protein. The heated reactant was filtered by diatomite to remove the enzyme, the filtrate was diluted by adding 2 times volume of acetone and then filtered to collect precipitated crude product solid which was recrystallized with water/acetone (volume ratio 1/2) to give 1.8 g pure white solid, i.e. compound (R)-1,2,3,4-tetrahydroisoquinoline-1-carboxylic acid ammonium salt, with 99.3% e.e. in 92.5% separation yield.

The NMR data of the resulted product were as follow:
$^1$H-NMR (400 MHz, $D_2O$, δ ppm): 3.07-3.10 (m, 2H, H-4), 3.45-3.66 (m, 2H, H-3), 4.95 (s, 1H, H-1), 7.29-7.54 (m, 4H, Ph), and the product was confirmed to be (R)-tetrahydroisoquinoline-1-carboxylic acid ammonium salt.

Example 3: Preparation of intermediate (R)-1,2,3,4-tetrahydroisoquinoline-1-carboxylic acid potassium salt 1.77 g DL-1,2,3,4-tetrahydroisoquinoline-1-carboxylic acid (0.01 mol) was dissolved in 5 mL $K_2HPO_4$—$KH_2PO_4$ buffer solution (adjusting pH to 8.2), and 2.61 g borane-tert-butylamine complex (0.03 mol) was added. Oxygen was inlet at a uniform speed, and 35.5 mg recombinant D-amino acid oxidase and 9 mg catalase were respectively added. Under the condition of stirring, the reaction was generated at 35° C. and the extent of the reaction was detected by HPLC. HPLC showed that after about 30 hours (S)-1,2,3,4-tetrahydroisoquinoline-1-carboxylic acid potassium salt was less than 1%. The reaction was stopped, and the solution was heated to 50-60° C. for more than half an hour to denature the enzyme protein. The heated reactant was filtered by diatomite to remove the enzyme, the filtrate was extracted by toluene (3×5 mL) and the toluene phases were collected to recycle tert-butylamine (2.1 g). The extracted water phase were diluted by adding 2 times volume of acetone, and then filtered to collect precipitated crude product solid which was recrystallized with water/acetone (volume ratio 1/2) to give 1.98 g pure white solid, i.e. compound (R)-1,2,3,4-tetrahydroisoquinoline-1-carboxylic acid potassium salt, with 99.2% e.e. in 91.8% separation yield.

Example 4: Preparation of intermediate (R)-1,2,3,4-tetrahydroisoquinoline-1-carboxylic acid sodium salt 1.77 g DL-1,2,3,4-tetrahydroisoquinoline-1-carboxylic acid (0.01 mol) was dissolved in 5 mL $NA_2HPO_4$—$NaH_2PO_4$ buffer solution (adjusting pH to 8.0), and 1.77 g borane-dimethyl amine complex (0.03 mol) was added. Oxygen was inlet at a uniform speed, and 53.5 mg recombinant D-amino acid oxidase and 9 mg catalase were respectively added. Under the condition of stirring, the reaction was generated at 37° C. and the extent of the reaction was detected by HPLC. HPLC showed that after about 32 hours (S)-1,2,3,4-tetrahydroisoquinoline-1-carboxylic acid sodium salt was less than 1%. The reaction was stopped, and the solution was heated to 50-60° C. for more than half an hour to denature the enzyme protein. The heated reactant was filtered by diatomite to remove the enzyme, the filtrate was diluted by adding 2 times volume of acetone and then filtered to collect precipitated crude product solid which was recrystallized with water/acetone (volume ratio 1/2) to give 1.86 g pure white solid, i.e. compound (R)-1,2,3,4-tetrahydroisoquinoline-1-carboxylic acid sodium salt, with 99.3% e.e. in 93.1% separation yield.

Example 5: Preparation of intermediate (R)-1,2,3,4-tetrahydroisoquinoline-1-carboxylic acid ammonium salt 1.77 g DL-1,2,3,4-tetrahydroisoquinoline-1-carboxylic acid (0.01 mol) was dissolved in 5 mL ammonia solution (adjusting pH to 8.5), and 3.45 g borane-triethylamine complex (0.03 mol) was added. Oxygen was inlet at a uniform speed, and 70.8 mg recombinant D-amino acid oxidase and 12 mg catalase were respectively added. Under the condition of stirring, the reaction was generated at 40° C. and the extent of the reaction was detected by HPLC. HPLC showed that after about 28 hours (S)-1,2,3,4-tetrahydroisoquinoline-1-carboxylic acid ammonium salt was less than 1%. The reaction was stopped, and the solution was heated to 50-60° C. for more than half an hour to denature the enzyme protein. The heated reactant was filtered by diatomite to remove the enzyme, the filtrate was diluted by adding 2 times volume of acetone and then filtered to collect precipitated crude product solid which was recrystallized with water/acetone (volume ratio 1/2) to give 1.81 g pure white solid, i.e. compound (R)-1,2,3,4-tetrahydroisoquinoline-1-carboxylic acid ammonium salt, with 99.3% e.e. in 93.3% separation yield.

Example 6: Preparation of intermediate (R)-1,2,3,4-tetrahydroisoquinoline-1-carboxylic acid potassium salt

1.77 g DL-1,2,3,4-tetrahydroisoquinoline-1-carboxylic acid (0.01 mol) was dissolved in 5 mL $K_2HPO_4$—$KH_2PO_4$ buffer solution (adjusting pH to 8.2), and 3.48 g borane-tert-butylamine complex (0.04 mol) was added. Oxygen was inlet at a uniform speed, and 47.5 mg recombinant D-amino acid oxidase and 12 mg catalase were respectively added. Under the condition of stirring, the reaction was generated at 35° C. and the extent of the reaction was detected by HPLC. HPLC showed that after about 35 hours (S)-1,2,3,4-tetrahydroisoquinoline-1-carboxylic acid potassium salt was less than 1%. The reaction was stopped, and the solution was heated to 50-60° C. for more than half an hour to denature the enzyme protein. The heated reactant was filtered by diatomite to remove the enzyme, the filtrate was diluted by adding 2 times volume of acetone, and then filtered to collect precipitated crude product solid which was recrystallized with water/acetone (volume ratio 1/2) to give 1.99 g white solid, i.e. compound (R)-1,2,3,4-tetrahydroisoquinoline-1-carboxylic acid potassium salt, with 99.1% e.e. in 92.3% separation yield.

Example 7: Preparation of (R)-1,2,3,4-tetrahydroisoquinoline-1-carboxylic acid 1.99 g (R)-1,2,3,4-tetrahydroisoquinoline-1-carboxylic acid potassium salt prepared according to Example 6 was dissolved in 5 mL pure water, and hydrogen chloride gas was inlet into the solution until pH value reached 2-3. 10 mL acetone was added and then filtered to collect precipitated solid which was dried to give 1.59 g (R)-1,2,3,4-tetrahydroisoquinoline-1-carboxylic acid, with 99.1% e.e. in 97% yield.

The NMR data of the product of this example were as follow: $^1H$ NMR (DMSO-d6, 400 MHz, δ ppm): 2.87-3.11 (m, 2H, $CH_2CH_2N$), 3.35-3.76 (m, 2H, $CH_2CH_2N$), 5.3 (d, 1H, CHCOOH), 7.24-7.35 (m, 4H, ArH), 9.45 (s, 1H, COOH), and the product was confirmed to be (R)-tetrahydroisoquinoline-1-carboxylic acid.

Example 8: Preparation of (1R)-2-[(tert-butyl) oxycarbonyl]-1,2,3,4-tetrahydroisoquinoline-1-carboxylic acid (compound 4A)

(R)-1,2,3,4-tetrahydroisoquinoline-1-carboxylic acid (80 g, 0.45 mol) dissolved in 845 mL tetrahydrofuran (THF) and Na₂C

O₃ (191.5 g, 1.8 mol) dissolved in 845 mL H₂O were mixed and cooled to 0° C. (Boc)₂O (108 g, 0.5 mol) dissolved in 280 mL tetrahydrofuran was dropwise added into the solution at 0° C. and then the system was stirred overnight. After the end of reaction, the system was extracted with ethylacetate (EA), and the extracted organic layers were merged, washed with NaCl saturated solution, dried over anhydrate sodium sulfate, and vacuum-evaporated to dryness. The dried residue was purified by silica gel column chromatography with PE/EA=1:1 as the eluent to give a white solid, i.e. compound 4A (106 g, 85% yield).

Example 9: Preparation of (1R)-1-hydroxymethyl-2-[(tert-butyl) oxycarbonyl]-1,2,3,4-tetrahydroisoquinoline (compound 4B)

Under the protection of N₂, BH₃ (2.0 M, 377 mL, 754 mmol) dissolved in THF was dropwise added into a solution of compound 4A (70.2 g, 0.25 mol) dissolved in 975 mL THF at 0° C. After the adding, the solution was stirred for 3 hours, and NaHCO₃ solution was dropwise added. After the end of reaction, the system was extracted with ethyl acetate, and the merged organic phases were washed with NaCl saturated solution, dried over anhydrate sodium sulfate, and vacuum-evaporated to dryness. The dried residue was purified by silica gel column chromatography with PE/EA=10:1~5:1 as the eluent, and concentrated to give a faint yellow oily product, i.e. compound 4B (53.3 g, 80% yield).

Example 10: Preparation of tert-butyl (1R)-1-[(1,3-dioxobenzo[c]azolidin-2-yl)methyl]-1,2,3,4- tetrahydroisoquinoline-2-carboxylate (compound 4C)

4C

DIAD (131 g, 0.65 mol) and triphenylphosphine (PPh₃) (170 g, 0.65 mol) were respectively added into a solution of compound 4B (85g, 0.32 mol) dissolved in 1L dichloromethane (DCM), and the mixture was stirred at room temperature for 30 min and then cooled to 0° C. Phthalimide (52.6 g, 0.36 mol) was added in batches, and the solution was warmed up to room temperature and stirred overnight. After the end of reaction, 1 L water was added, and the solution was extracted with EA, and the merged organic phases were respectively washed with water and saturated salt water, dried over anhydrate sodium sulfate, and vacuum-evaporated to dryness. The dried residue was purified by silica gel column chromatography with PE/EA=200:1~20:1 as the eluent, and concentrated to give a white solid, i.e. compound 4C (90.0 g, 70 % yield)).

Example 11: Preparation of tert-butyl (1R)-1-[(cyclohexylcarbonylamino) methyl]-1,2,3,4-tetrahydro isoquinoline-2-carboxylate (compound 4F)

60 mL hydrazine hydrate was added into a solution of compound 4C (61 g, 0.15 mol) dissolved in 360 mL ethanol. The mixture was refluxed for 40 min, cooled to room temperature, and then concentrated. 360 mL EA was added, and the solution was stirred for 30 min and filtered to remove the generated solid. The filtrate was concentrated to give a yellow oily compound 4D (41.4 g) used directly in the next step.

Compound 4D (41.4 g, 0.15 mol) was dissolved in 450 mL THF, and 2 mol/L NaOH solution (300 mL, 600 mmol) was added, and the system was cooled to 0° C. Then a solution of compound 4E (27 g, 0.18 mol) dissolved in 150 mL THF was dropwise added and the solution was stirred for 2 hours, warmed up to room temperature and stirred overnight. After the end of reaction, 600 mL water was added, and the solution was extracted with EA, and the merged organic phases were respectively washed with water and NaCl saturated solution, dried over anhydrate sodium sulfate, and vacuum-dried. The dried residue was purified by silica gel column chromatography with PE/EA=20:1~10:1 as the eluent, and concentrated to give a white solid, i.e. compound 4F (40.5 g, 70% overall yield for two steps).

Example 12: Preparation of (R)-Praziquantel

Compound 4F (90 g, 0.24 mol) and HCl/EA solution (1.9 L) were stirred at room temperature for 2 hours and checked by LC-MS. After the end of reaction, the solvent was evaporated off. The residue of evaporation was dissolved in DCM, and the solution was respectively washed with saturated sodium bicarbonate (NaHCO$_3$) and NaCl saturated solution, and concentrated to give a white solid 4G (66.9 g). The white solid 4G (66.9 g, 0.24 mol) was dissolved in 250 mL dichloromethane, and then chloroacetyl chloride (30.3 g, 0.26 mol) dissolved in 130 mL dichloromethane and 50% NaOH solution (77 mL) were added, respectively. After stirring for 30 min, benzyl triethyl ammonium chloride (TEBAC, 5.5 g, 0.024 mol) was added, and the mixture was heated to reflux for 2 hours. After the end of reaction, 380 mL water was added, and the mixture was extracted with dichloromethane. The merged organic phases were respectively washed with water for 2 times, with 5% hydrochloric acid solution and with saturated salt water, and dried over anhydrate sodium sulfate. After evaporating off the solvent, the residue was purified by silica gel column chromatography with PE/EA=20:1~5:1 as the eluent, and concentrated to give a product, i.e. (R)-praziquantel.

The NMR data of (R)-praziquantel were as follow: $^1$H NMR (300 MHz, DMSO-d6): δ 1.26-1.30 (m, 3H), 1.46-1.63 (m, 3H), 1.72-1.88 (m, 5H), 2.43-2.56 (m, 1H), 2.77-2.87 (m, 2H), 2.90-3.25 (m, 2H), 3.84-4.10 (m, 1H), 4.35-4.49 (m, 1H), 4.79-4.87 (m, 2H), 5.15-5.18 (d, 1H), 7.17-7.19 (d, 2H), 7.24-7.28 (d, 2H).

Example 13: Preparation of (R)-praziquantel crystal form 0.5 g concentrated product obtained according to Example 12 was dissolved in 3 g acetonitrile (CH$_3$CN) at 20° C. The solution was filtered, and the filtrate was kept. 1.5 g acetone and 10 g toluene were added into the filtrate, respectively. Let the system stand at 20° C. overnight, and then it was filtered to give 0.412 g white solid, i.e. crystal form of (R)-praziquantel. The yield was 82.4%, the purity was 99.1%, and the e.e. value was 99.5%. The XRD pattern thereof was as illustrated in FIG. 1.

Example 14: Preparation of R-praziquantel crystal form 0.5 g concentrated product obtained according to Example 12 was dissolved in 3.69 g tetrahydrofuran at 20° C. The solution was filtered, and the filtrate was kept. 8.47 g n-heptane was added into the filtrate, and the system was cooled to 10° C. Let the system stand overnight, and then it was filtered to give 0.466 g white solid, i.e. crystal form of (R)-praziquantel. The yield was 93.2%, the purity was 99.3%, and the e.e. value was 99.2%. The XRD pattern thereof was as illustrated in FIG. 1.

Example 15: Preparation of (R)-praziquantel crystal form 0.5 g concentrated product obtained according to Example 12 was dissolved in 3 g acetic acid isopropyl ester and 10 g ethanol, and the solution was heated to 60° C. and filtered, and the filtrate was kept. 8.6 g cyclohexane was added into the filtrate, and the system was cooled to 30° C. Let the system stand overnight, and then it was filtered to give 0.482 g white solid, i.e. crystal form of (R)-praziquantel. The yield was 96.4%, the purity was 99.4%, and the e.e. value was 99.3%. The XRD pattern thereof was as illustrated in FIG. 1.

Example 16: Characterization of crystal form of (R)-praziquantel

1. Both the crystal form of (R)-praziquantel and the crystal form of praziquantel made previously were analyzed by powder X-ray diffraction (XRPD) analysis; the crystal form of (R)-praziquantel was also analyzed by infrared absorption (IR) method, differential scanning calorimetry (DSC) and optical rotation determination, wherein:

The preparation method of praziquantel crystal form made previously was as follow: 30 mL methanol and 60 mL water were mixed at room temperature (20° C.), and 0.5 g praziquantel sample was added to the solution and fully dissolved. The solution was heated up to 40° C. and dried under the condition of vacuum to give a white solid, i.e. praziquantel crystal form.

XRPD measurement employed an EMPYREAN X-ray Diffractometer with CuKα radiation from PANALYTICAL INC. About 10 mg sample was distributed evenly onto a monocrystalline silicon sample pan, and the XRPD measurement was carried out using the parameters in the following table:

| | |
|---|---|
| Start Position [°2Th.]: 3.0012 | End Position [°2Th.]: 39.9999 |
| Step Size [°2Th.]: 0.0130 | Scan Step time [s]: 20.4000 |
| K-Alpha1 [Å]: 1.54060 | K-Alpha2 [Å]: 1.54443 |
| Generator Settings: 40 mA, 45 kV | |

Infrared absorption (IR) measurement employed an infrared detector from SHIMADZU, and employed potassium bromide-pellet technique in which blank KBr plates and sample-KBr plates were respectively prepared, and IR measurement was carried out using the parameters in the following table:

| | |
|---|---|
| Measuring Mode: % Transmittance | Apodization: Happ-Genzal |
| No. of Scans: 40 | Resolution: 4 $cm^{-1}$ |
| Range: 4000-400 $cm^{-1}$ | |

DSC measurement was carried out on a TAQ 200 differential scanning calorimeter, and the test parameters were as follow:

| DSC | |
|---|---|
| Sample Pan | Aluminum Pan, Lid Crimped |
| Temperature/° C. | 25-200° C. |
| Scanning Rate/(° C./min) | 10 |
| Protective Gas | Nitrogen |

The above-mentioned crystal form of (R)-praziquantel was characterized in that, the optical rotation at 20° C.: $[\alpha]_D = -140.12°$ ($CH_3OH$).

The differential scanning calorimeter showed that the melting point of the crystal form of (R)-praziquantel was 108.83° C.

Figure 2:
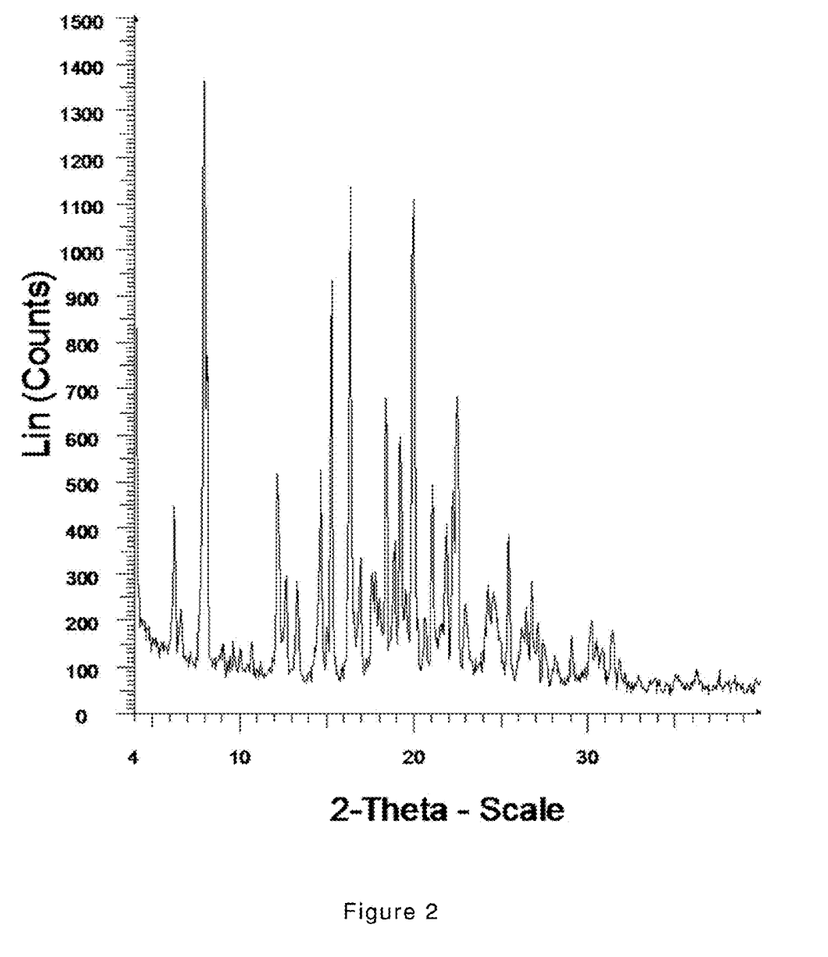
FIG. 2 is an X-ray powder diffraction spectrum of praziquantel crystal form.
Figure 3:
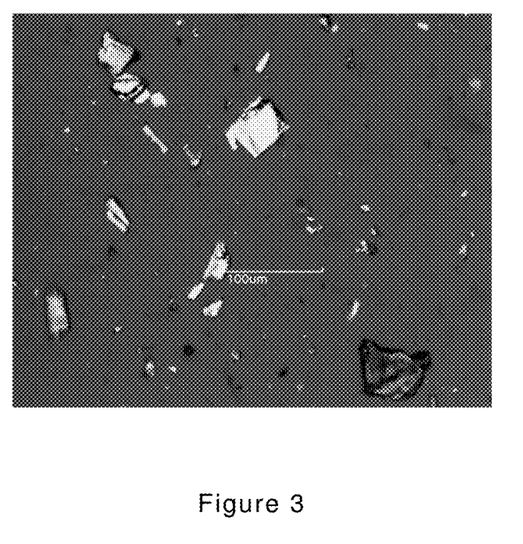
FIG. 3 is the (R)-praziquantel crystal form observed under polarization microscope.
Figure 4:
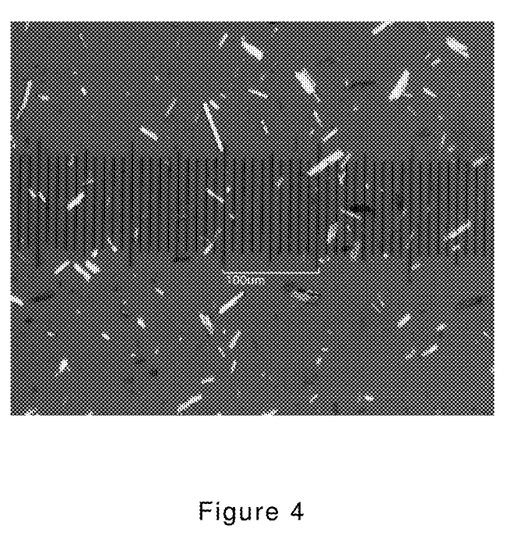
FIG. 4 is the praziquantel crystal form observed under polarization microscope.
Figure 6:
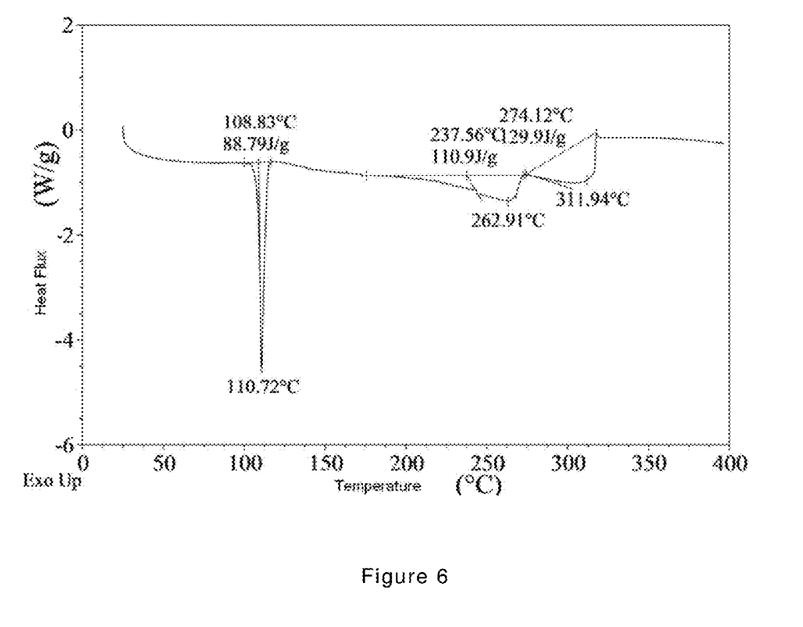
FIG. 6 is a DSC thermogram of (R)-praziquantel crystal form.

The XRPD patterns of the crystal form of (R)-praziquantel and praziquantel were as illustrated in FIG. 1 and FIG. 2, respectively. The XPRD diffraction peak data of (R)-praziquantel crystal form is listed in Table 1, and the XPRD data comparison of the strongest 10 diffraction peaks of the crystal forms between (R)-praziquantel and praziquantel are showed in Table 2; when observed under polarizing optical microscope, all samples of (R)-praziquantel crystal form demonstrated birefringence phenomenon in the form of tabular crystal or long rod-like crystal, referring to FIG. 3, while praziquantel crystal form showed short and small rod-like crystal, referring to FIG. 4; the IR spectrum and DSC thermogram of crystal form of (R)-praziquantel are illustrated in FIG. 5 and FIG. 6, respectively.

TABLE 1

XRPD data of (R)-praziquantel crystal form

| Caption | Angle 2-Theta ° | d value Angstrom | Intensity Count | Intensity % % |
|---|---|---|---|---|
| 1 | 6.929 | 12.74616 | 855 | 39.2 |
| 2 | 8.329 | 10.60733 | 2151 | 98.6 |
| 3 | 8.667 | 10.19385 | 212 | 9.7 |
| 4 | 12.82 | 6.8995 | 166 | 7.6 |
| 5 | 13.421 | 6.59225 | 336 | 15.4 |
| 6 | 14.08 | 6.28507 | 444 | 20.4 |
| 7 | 15.076 | 5.87211 | 2181 | 100 |
| 8 | 15.724 | 5.63121 | 1086 | 49.8 |
| 9 | 16.611 | 5.33251 | 1347 | 61.8 |
| 10 | 17.4 | 5.09254 | 1629 | 74.7 |
| 11 | 17.875 | 4.95836 | 783 | 35.9 |
| 12 | 18.241 | 4.85966 | 373 | 17.1 |
| 13 | 18.952 | 4.67892 | 462 | 21.2 |
| 14 | 19.795 | 4.48152 | 2110 | 96.7 |
| 15 | 20.591 | 4.31006 | 330 | 15.1 |
| 16 | 21.627 | 4.10583 | 560 | 25.7 |
| 17 | 21.899 | 4.05534 | 1510 | 69.2 |
| 18 | 23.034 | 3.8581 | 207 | 9.5 |
| 19 | 23.781 | 3.73849 | 888 | 40.7 |
| 20 | 24.271 | 3.66415 | 1011 | 46.4 |
| 21 | 25.419 | 3.50128 | 136 | 6.2 |
| 22 | 25.798 | 3.45069 | 94 | 4.3 |
| 23 | 27.43 | 3.24889 | 510 | 23.4 |
| 24 | 27.822 | 3.20408 | 136 | 6.2 |
| 25 | 28.491 | 3.1303 | 173 | 7.9 |
| 26 | 29.022 | 3.0742 | 231 | 10.6 |
| 27 | 29.269 | 3.04888 | 184 | 8.4 |
| 28 | 30.266 | 2.95061 | 109 | 5 |

TABLE 1-continued

XRPD data of (R)-praziquantel crystal form

| Caption | Angle 2-Theta ° | d value Angstrom | Intensity Count | Intensity % % |
|---|---|---|---|---|
| 29 | 30.561 | 2.92283 | 110 | 5 |
| 30 | 30.881 | 2.89324 | 176 | 8.1 |
| 31 | 32.4 | 2.76103 | 153 | 7 |
| 32 | 33.727 | 2.65539 | 276 | 12.7 |
| 33 | 34.239 | 2.61683 | 85 | 3.9 |
| 34 | 36.379 | 2.46765 | 151 | 6.9 |
| 35 | 38.423 | 2.34093 | 113 | 5.2 |
| 36 | 39.474 | 2.28097 | 682 | 31.3 |

TABLE 2

Data Comparison of the 10 strongest diffraction peaks of the crystal forms between (R)-praziquantel and praziquantel

| Caption | Angle 2-Theta ° | d value Angstrom | Intensity Count | Intensity % % |
|---|---|---|---|---|
| XRPD data of the strongest 10 diffraction peaks of (R)-praziquantel crystal form | | | | |
| 1 | 6.929 | 12.74616 | 855 | 39.2 |
| 2 | 8.329 | 10.60733 | 2151 | 98.6 |
| 7 | 15.076 | 5.87211 | 2181 | 100 |
| 8 | 15.724 | 5.63121 | 1086 | 49.8 |
| 9 | 16.611 | 5.33251 | 1347 | 61.8 |
| 10 | 17.4 | 5.09254 | 1629 | 74.7 |
| 14 | 19.795 | 4.48152 | 2110 | 96.7 |
| 17 | 21.899 | 4.05534 | 1510 | 69.2 |
| 19 | 23.781 | 3.73849 | 888 | 40.7 |
| 20 | 24.271 | 3.66415 | 1011 | 46.4 |
| XRPD data of the 10 strongest diffraction peaks of praziquantel crystal form | | | | |
| 3 | 7.906 | 11.17382 | 1367 | 100 |
| 9 | 12.147 | 7.28062 | 514 | 37.6 |
| 12 | 14.628 | 6.05086 | 521 | 38.1 |
| 13 | 15.24 | 5.80895 | 935 | 68.4 |
| 14 | 16.316 | 5.42843 | 1136 | 83.1 |
| 19 | 18.402 | 4.81731 | 676 | 49.5 |
| 21 | 19.246 | 4.60806 | 595 | 43.5 |
| 23 | 19.958 | 4.44526 | 1110 | 81.2 |
| 25 | 21.091 | 4.20883 | 492 | 36 |
| 29 | 22.495 | 3.94929 | 683 | 50 |

Example 17

The measurement of solubility of (R)-praziquantel and praziquantel crystal forms in water and simulated gastric-intestinal fluid, which was described as below:

About 2 mg of each compound was respectively placed in several glass vials, and pure water, simulated gastric fluid (SGF), simulated intestinal fluid under fasted status (FaSSIF), and simulated intestinal fluid under fed status (FeSSIF) were respectively added to prepare a final sample concentration of 2 mg/mL. The samples were sonicated to be dispersed evenly and then rotated 360 degree-wise to equilibrate for 18 hours at room temperature (25° C.). After the equilibration, the samples were visually inspected to check whether they were completely dissolved, and then filtrated through 45 μm filter membrane. The resulted filtrate was diluted with suitable solvent for HPLC analysis. Two duplicate samples of each matrix were taken into analysis, and the results are listed in Table 3.

TABLE 3

Comparison of solubility between (R)-praziquantel and praziquntel crystal forms in different conditions

| | Average solubility (mg/mL) | |
|---|---|---|
| Media | (R)-prazqiuantel crystal form | Praziquantel crystal form |
| Water | 0.305 | 0.199 |
| SGF | 0.303 | 0.192 |
| FeSSIF | 0.433 | 0.313 |
| FaSSIF | 0.302 | 0.193 |

Example 18

Comparison of anti-*schistosoma japonicum* activity between the crystal forms of (R)-praziquantel and praziquantel in in vitro culture experiment, which was specifically as follow:

Raw powders of (R)-praziquantel and praziquantel were respectively dissolved in PEG-400 to prepare 2 wt % drug solution. An aliquot of the drug solution (5-50 μL) was transferred and diluted with culture medium (prepared by Tyrode's solution and calf serum at 9:1, pH 7.4, containing 100 IU/mL penicillin and 100 IU/mL streptomycin) to a desired concentration (0.0001-100 μg/mL). Japanese white rabbits and Kunming hybrid mice were infected with cercariae of *schistosoma japonicum* for 5-8 weeks. Under aseptic condition, mesenteric vein and liver were perfused with normal saline, and the recovered schistosomes were washed with Tyrode's solution twice and then transferred into culture medium and cultured at 37° C. for use. Intact, active and paired worms were selected and transferred at 1 pair/flask into Carlsberg's culture flasks filled with 4 mL culture solutions containing different concentrations of (R)-praziquantel and praziquantel, and cultured at 37° C. for different time periods. The worm activity and changes on body surface were observed under stereomicroscope and inverted microscope at room temperature. The active levels of worm were defined as below:

++++ Worm twitching or rolling intensively;
+++ Worm wriggling or paroxysmally trembling frequently;
++ Worm migrating freely with enterocinesia;
+ Movement of worm weakened and enterocinesia disappeared;
± No movement of worm was observed under stereomicroscope (×30), and slight movement of mouth and ventral suckers were observed under inverted microscope (×250);
− No movement of worm was observed under inverted microscope (×250);

wherein +++ and ++++ refer to worm excitement; ++ refers to normal worm activity; + and ± refers to inhibition of worm activity; worm was considered to death if the result was still negative after observing for 5 min. The results are shown in Table 4.

TABLE 4

Comparsion of in vitro activity[1] against *schistosoma japonicum* of (R)-praziquantel and praziquantel crystal forms

| | (R)-praziquantel | Praziquantel |
|---|---|---|
| [2]IC$_{50}$ ± [3]L$_{95}$ | 0.008 ± 0.004 | 0.042 ± 0.018* |

[1]Activity: spasm or paralysis of *schistosoma japonicum* after administration were considered as active;
[2]IC$_{50}$: median inhibitory concentration, unit: μM;
[3]L$_{95}$: 95% confidence interval.
(*P < 0.01)

Example 19

Evaluation of in vivo anti-parasitic activity of (R)-praziquantel crystal form in SD rats infected with *clonorchis sinensis*, which was specifically as follow:

Each of total 29 SD rats with 200~300 g of body weight were given with 30 metacercariae of *clonorchis sinensis* via gavage intragastrically. On Day 35 post infection, fecal smear examination was conducted, and worm eggs of *clonorchis sinensis* were found in all of the smears which confirmed successful modeling. Subsequently, the rats were randomly divided into (R)-praziquantel group (n=14) and blank control group (n=15). (R)-praziquantel was formulated with PEG-400 to a concentration of 2%, and the rats were dosed at 100 mg/kg via gavage twice a day for two days of continuous treatment, while the rats of the control group were given the same volume of PEG-400 only. Seven days after the end of the treatment, worms are recovered from the bile ducts under sterility condition. The averaged number of recovered worms, mean recovery rate of worms and cure rate after treatment were calculated, and the results are shown in Table 5.

TABLE 5

Results of (R)-praziquantel crystal form in the treatment of clonorchiasis in rat

| Grouping | No. of Animal | No. of Cured animal | Cure rate, % | No. of Average of recovered worm, $\bar{X} \pm SD$ | Mean recovery rate of worms, % |
|---|---|---|---|---|---|
| (R)-praziquantel | 14 | 14 | 100 | 0 | 0 |
| Blank control | 15 | 0 | 0 | 8.45 ± 9.57* | 28.22* |

(*P < 0.01)

Example 20

Figure 7:
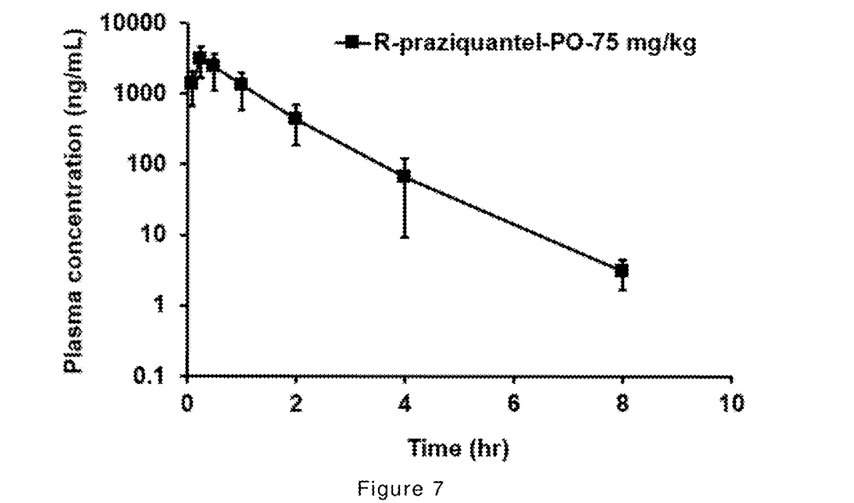
FIG. 7 is a concentration-time curve in rat plasma after oral administration of (R)-praziquantel crystal form.

Investigation on characteristic of the plasma concentrations of (R)-praziquantel crystal form in rats after oral administration, which was specifically as follow:

Adequate amount of (R)-praziquantel powder was weighed and suspended in 0.5% methylcellulose (MC) solution to form a suspension of 7.5 mg/mL, and then vortexed and sonicated until mixed homogeneously. The rats (N=3) were intragastrically administrated with the drug at 10 mL/kg (i.e. 75 mg/kg). Rat blood samples were collected at predose, and 5 min, 15 min, 30 min, 1 h, 2 h, 4 h, 8 h and 24 h after dose, and the blood samples were centrifuged to obtain plasma samples for drug concentration analysis by HPLC-MS. The results are shown in FIG. 7. After rats were given with the drug at a single oral-dose of 75 mg/kg, the biological disposition was as follow: the time to reach peak plasma concentration of the drug was 15 min, and the peak plasma concentration was 3132±1440 ng/mL, the terminal half-life was 0.89±1.9 h, and the area under plasma concentration-time curve was 3572±1793 h·ng/mL.

Example 21

Comparison of characteristics of plasma concentrations after oral administration of (R)-praziquantel and praziquantel crystal forms in mice. The specific method was as follow:

Adequate amount of (R)-praziquantel or praziquantel powder was weighed and suspended in 0.5% methylcellulose (MC) to form a suspension of 10 mg/mL, and then vortexed and sonicated until mixed homogeneously. The rats (N=3) were intragastrically administrated with the drugs at 10 mL/kg (i.e. 100 mg/kg). Mouse blood samples were collected at predose, and 5 min, 15 min, 30 min, 1 h and 2 h after dose, and the blood samples were centrifuged to obtain plasma samples for drug concentration analysis by HPLC-MS. The results showed that, after orally giving the mice with (R)-praziquantel and praziquantel respectively at 100 mg/kg in the two groups of animals, the time to reach peak plasma concentration of (R)-praziquantel both were 15 minutes, the peak plasma concentrations of the drug were 1290 ng/mL and 464 ng/mL respectively, and the areas under concentration-time curves were 667 h·ng/mL and 208 h·ng/mL respectively (see FIG. 8). It was thus evident that, after giving the mice with the same oral dose of (R)-praziquantel and praziquantel, the plasma exposure and the peak concentration of the active component, e.g. the (R)-praziquantel in (R)-praziquantel crystal form group were apparently higher than those in praziquantel crystal form group.

The embodiments described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

The invention claimed is:

1. A crystal form of (R)-praziquantel, wherein the X-ray diffraction pattern (CuKα radiation) of the crystal form at 25° C. shows the following diffraction peaks: 2-Theta=6.9±0.2°, 8.3±0.2°, 13.4±0.2°, 14.1±0.2°, 15.1±0.2°, 15.7±0.2°, 16.6±0.2°, 17.4±0.2°, 17.9±0.2°, 18.2±0.2°, 19.0±0.2°, 19.8±0.2°, 20.6±0.2°, 21.9±0.2°, 23.8±0.2°, 24.3±0.2°, 27.4±0.2°, 28.5±0.2°, 29.0±0.2°, 30.9±0.2°, 33.7±0.2°, and 39.5±0.2° or d=12.74±0.20 Å, 10.61±0.20 Å, 6.59±0.20 Å, 6.29±0.20 Å, 5.87±0.20 Å, 5.63±0.20 Å, 5.33±0.20 Å, 5.09±0.20 Å, 4.96±0.20 Å, 4.86±0.20 Å, 4.68±0.20 Å, 4.48±0.20 Å, 4.31±0.20 Å, 4.06±0.20 Å, 3.74±0.20 Å, 3.66±0.20 Å 3.25±0.20 Å, 3.13±0.20 Å, 3.07±0.20 Å, 2.89±0.20 Å, 2.66±0.20 Å, and 2.28±0.20 Å.

2. The crystal form according to claim 1, wherein the X-ray diffraction pattern (CuKα radiation) of the crystal form at 25° C. further shows the following five diffraction peaks: 2-Theta=8.67±0.2°, 23.0±0.2°, 25.4±0.2°, 27.8±0.2°, and 32.4±0.2° or d=10.19±0.20 Å, 3.86±0.20 Å, 3.50±0.20 Å, 3.20±0.20 Å, and 2.76±0.20 Å.

3. The crystal form according to claim 2, wherein the X-ray diffraction pattern is shown in FIG. 1.

4. The crystal form according to claim 1, wherein the differential scanning calorimetry thermogram shows an absorption peak at 111° C.±3° C., wherein the melting point of the crystal form is 109° C.±2° C. and the optical rotation of the crystal form, $[\alpha]_D$, at 20° C. is −140.12° (CH$_3$OH).

5. The crystal form according to claim 1, wherein the infrared absorption spectrum shows absorption peaks at 3460 cm$^{-1}$, 3277 cm$^{-1}$, 3065 cm$^{-1}$, 3048 cm$^{-1}$, 3021 cm$^{-1}$, 3003 cm$^{-1}$, 2932 cm$^{-1}$, 2853 cm$^{-1}$, 2660 cm$^{-1}$, 1651 cm$^{-1}$, 1645 cm$^{-1}$, 1622 cm$^{-1}$, 1576 cm$^{-1}$, 1570 cm$^{-1}$, 1558 cm$^{-1}$, 1541 cm$^{-1}$, 1533 cm$^{-1}$, 1522 cm$^{-1}$, 1506 cm$^{-1}$, 1497 cm$^{-1}$, 1489 cm$^{-1}$, 1472 cm$^{-1}$, 1456 cm$^{-1}$, 1437 cm$^{-1}$, 1418 cm$^{-1}$ 1387 cm$^{-1}$, 1364 cm$^{-1}$, 1339 cm$^{-1}$, 1323 cm$^{-1}$, 1296 cm$^{-1}$, 1285 cm$^{-1}$, 1263 cm$^{-1}$, 1254 cm$^{-1}$, 1242 cm$^{-1}$, 1217 cm$^{-1}$, 1190 cm$^{-1}$, 1175 cm$^{-1}$, 1136 cm$^{-1}$ 1121 cm$^{-1}$, 1082 cm$^{-1}$, 1074 cm$^{-1}$, 1061 cm$^{-1}$, 1042 cm$^{-1}$, 1032 cm$^{-1}$, 997 cm$^{-1}$, 972 cm$^{-1}$, 962 cm$^{-1}$, 939 cm$^{-1}$, 924 cm$^{-1}$, 907 cm$^{-1}$, 893 cm$^{-1}$, 854 cm$^{-1}$, 831 cm$^{-1}$, 793 cm$^{-1}$, 756 cm$^{-1}$, 731 cm$^{-1}$, 723 cm$^{-1}$, 689 cm$^{-1}$, 648 cm$^{-1}$, 631 cm$^{-1}$, 594 cm$^{-1}$ 575 cm$^{-1}$, 546 cm$^{-1}$, 527 cm$^{-1}$, 509 cm$^{-1}$, 486 cm$^{-1}$, 473 cm$^{-1}$, 457 cm$^{-1}$, 442 cm$^{-1}$ and 409 cm$^{-1}$, and further wherein the absorption peak positions vary within ±2 cm$^{-1}$.

6. The crystal form according to claim 1, wherein the solubility in water at 25° C. and the solubility in simulated gastrointestinal fluid at 25° C. ranges from 0.30 to 0.43 mg/mL.

7. A pharmaceutical composition comprising the crystal form according to claim 1 and a pharmaceutically acceptable carrier.

8. The pharmaceutical composition according to claim 7, wherein the pharmaceutical composition is formulated as a tablet, a capsule, a pill, a granule, a syrup, an aqueous injection, a powdered injection, a premix, an aerosol, a suspension, a solvent or a drug rod.

9. A method for treating a parasitic disease in a subject, comprising administering to the subject an effective amount of the crystal form according to claim 1, wherein the parasitic disease is selected from the group consisting of clonorchiasis, an infection due to *clonorchis sinensis*; and *schistosomiasis japonicum*, an infection due to *schistosoma japonicum*.

10. A method for preparing the crystal form according to claim 1, comprising the steps of:
(i) dissolving (R)-praziquantel in an organic solvent at a temperature in the range of 20° C.-60° C., wherein the organic solvent is selected from the group consisting of ethyl acetate, isopropyl acetate, methanol, ethanol, tetrahydrofuran and acetonitrile, or a mixture thereof;
(ii) filtering the above solution;
(iii) retaining the filtrate; and
(iv) isolating the crytal form of (R)-praziquantel via crystallization at a temperature in the range of 10° C.-30° C.; or
(v) isolating the crystal form of (R)-praziquantel via antisolvent addition or solvent removal under vacuum, wherein the antisolvent is selected from the group consisting of water, toluene, n-heptane, cyclohexane and acetone, or a mixture thereof.

11. The method according to claim 10, further comprising the step of:
(i) reacting a compound of the formula 4H:

4H with benzyltriethylammonium chloride in dichloroethane to provide (R)-praziquantel of the formula:

* * * * *